(12) United States Patent
Koller et al.

(10) Patent No.: US 7,361,162 B2
(45) Date of Patent: Apr. 22, 2008

(54) MEDICINAL SYRINGE WITH PISTON STOPPER WITHDRAWAL AND ROTATION-LIMITING MEANS

(75) Inventors: Horst Koller, Engelburg (CH); Markus Steigenberger, Bischofsheim (DE); Karl Mosimann, Wuppenau (CH); Thomas Kadur, Engelburg (CH)

(73) Assignee: Schott AG, Mainz (DE)

( * ) Notice: Subject to any disclaimer, the term of this patent is extended or adjusted under 35 U.S.C. 154(b) by 57 days.

(21) Appl. No.: 10/705,074

(22) Filed: Nov. 10, 2003

(65) Prior Publication Data

US 2004/0260248 A1 Dec. 23, 2004

(30) Foreign Application Priority Data

Nov. 11, 2002 (DE) .................. 102 52 220

(51) Int. Cl.
*A61M 5/315* (2006.01)
(52) U.S. Cl. .............. 604/227; 604/220; 604/218; 604/187; 604/181
(58) Field of Classification Search .......... 604/218, 604/220, 223, 227, 228, 110, 181, 187
See application file for complete search history.

(56) References Cited

U.S. PATENT DOCUMENTS

| 3,747,812 | A | * | 7/1973 | Karman et al. ............. 222/387 |
| 4,072,149 | A | | 2/1978 | Tischlinger |
| 4,267,846 | A | | 5/1981 | Kontos |
| 4,562,844 | A | * | 1/1986 | Carpenter et al. .......... 600/488 |
| 4,592,746 | A | * | 6/1986 | Burkholder et al. ........ 604/220 |
| 4,711,637 | A | | 12/1987 | Leigh et al. |
| 4,909,788 | A | | 3/1990 | Egolf |

(Continued)

FOREIGN PATENT DOCUMENTS

DE 331326 1/1921

(Continued)

OTHER PUBLICATIONS

Din Iso 11040-4, Vorgefuellte Spritzen,"Teil 4: Spritzenzylinder Aus Glas Fuer Injektionspraeparate" Aug. 1996. Bilingual.

*Primary Examiner*—Kevin C. Sirmons
*Assistant Examiner*—Laura C. Schell
(74) *Attorney, Agent, or Firm*—Michael J. Striker

(57) ABSTRACT

The syringe is formed according to DIN ISO 11040 and has a syringe barrel (1) with a syringe head (1*a*) formed on one end and a grip plate (4) formed at the other open end. An elastomeric piston stopper (6) is insertable in this open end, which is movable back and forth and which has a cruciform-cross-sectioned piston rod (7) screwed into it. A stop element, which reduces the interior diameter of the syringe barrel, is provided at the open end of the syringe barrel to perform a back-stop function, i.e. to prevent unintended withdrawal of the piston stopper. For this purpose a plastic part (2) connected to the grip plate (4) is provided with snap catches (3), which snap onto the inner side of the syringe barrel (1). These snap-catches (3) prevent the piston rod (7) from being rotated out of the piston stopper and the piston stopper (6) from being withdrawn from the syringe barrel. At the same time the finger support is enlarged.

8 Claims, 3 Drawing Sheets

U.S. PATENT DOCUMENTS

| | | |
|---|---|---|
| 5,084,017 A | 1/1992 | Maffetone |
| 5,325,032 A * | 6/1994 | Thompson et al. .... 318/586.13 |
| 5,554,133 A | 9/1996 | Haffner et al. |
| 5,700,247 A * | 12/1997 | Grimard et al. ............ 604/220 |
| 5,803,918 A * | 9/1998 | Vetter et al. ................ 604/110 |
| 5,997,511 A * | 12/1999 | Curie et al. ................. 604/195 |
| 6,296,625 B1 | 10/2001 | Vetter et al. |

FOREIGN PATENT DOCUMENTS

| | | |
|---|---|---|
| DE | 43 31 137 A1 | 11/1994 |
| DE | 100 36 829 A1 | 2/2002 |
| WO | WO 01/64266 * | 9/2001 |

* cited by examiner

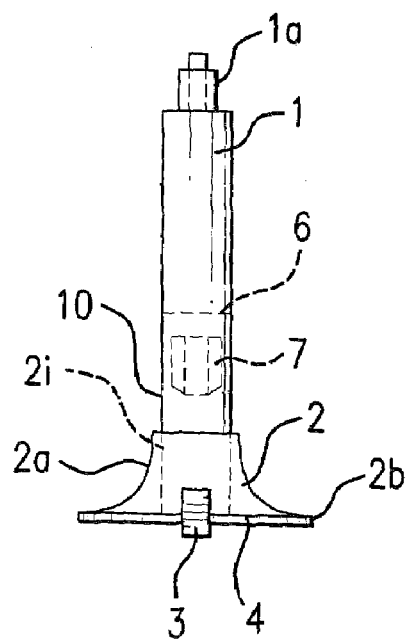
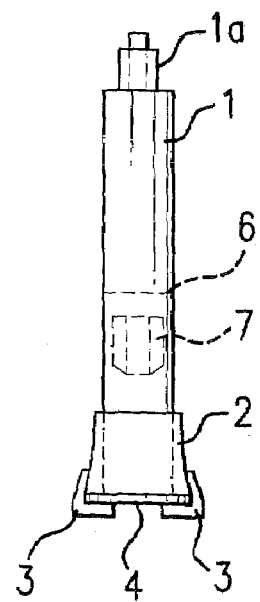
FIG.1  FIG.2
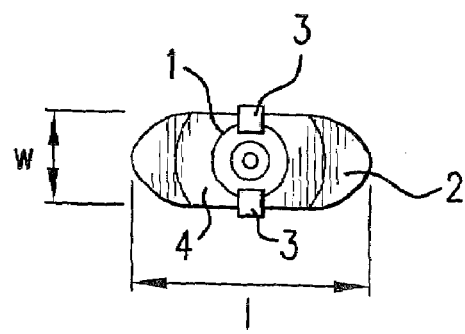
FIG.3

MEDICINAL SYRINGE WITH PISTON STOPPER WITHDRAWAL AND ROTATION-LIMITING MEANS

BACKGROUND OF THE INVENTION

1. Field of the Invention

The present invention relates to a medicinal syringe, comprising a syringe barrel made of glass or plastic formed with a syringe head, in which either a hollow syringe needle can be integrated or which has a Luer cone, and with a grip plate at its open end;

an elastomeric piston stopper, which is insertable in the syringe barrel, and which has a threaded blind hole for screw connection with a piston rod having a cruciform cross-section; and a stop for preventing unintended withdrawal of the piston stopper.

2. Description of the Related Art

It is known to use ampoules and injector bottles for parenteral administration of liquid pharmaceutical products. A medicinal syringe combined with a suitable hollow syringe needle is required for injecting the products contained in these bottles. That means that the liquid pharmaceutical product must be transfer into the medicinal syringe prior to its end use. This process is not only time consuming, but it enables a large number of impurity sources.

In order to guarantee a reliable use of pharmaceutical products, pre-filled one-time-use syringes are available commercially. They permit a rapid injection of the product that they contain after a comparatively simple manipulation or handling. This sort of pre-filled syringe has a syringe barrel made from glass or plastic with a syringe head formed on it, in which either a syringe needle is integrated or which has a Luer connecting cone of a conical connection, if necessary a lockable cone connection (Luer lock). A grip plate is mounted on the other open end of the syringe barrel, either formed in one piece with it or put on it as a separate part. An elastomeric piston stopper is slidable through the open end of the syringe barrel. The piston stopper has a threaded blind hole, in which a piston rod with a threaded front end is screwable in various embodiments. The aforementioned one-time-use syringe, also called a ready-made syringe, with a syringe body made of glass, is described in Norm DIN ISO 11040, in which, for example, the syringe barrel is described in part 4. The elastomeric standard piston stopper and standard piston rod made of plastic with a cruciform cross section are described in part 5.

Pre-filled one-time-use syringes made from plastic are similarly components of standard design and described in numerous references. Especially they have a similar structure, which relates to the piston stopper and the piston rod.

The present invention is based on syringes of the above-described type, which have been put on the market and used to a great extent. The invention is also applicable to syringes, which are not pre-filled, and which, as mentioned above, draw their contents from a bottle in application.

In order to guarantee a problem-free use of the above-describes syringes, other structural features are required because the above-described basic features.

In order to prevent an unintended withdrawal of the piston stopper from the syringe cylinder during the storage, preparation and/or use of the above-described syringe, and/or to guarantee that the uppermost sealing ring of the piston stopper always remains in the syringe barrel, it is necessary to insert a so-called backstop in the syringe body, typically a stop which reduces the diameter of the syringe barrel at its open end. Otherwise the contamination seal of the pre-filled syringe would not be guaranteed.

The state of the art provides different embodiments for this stop.

In the known one-time-use syringe according to DE 100 36 829 A the stop is formed by a ring-shaped constriction of the syringe barrel, which is provided in the filled syringe barrel after insertion of the piston stopper, in order to not prevent insertion of the piston stopper after filling of the syringe.

DE 43 31 137 A provides a stop element mounted on the grip plate end of the syringe on a finger support with enlarged supporting surface in relation to the DIN grip plate. The stop element has at least one projection extending into the syringe barrel, against which the piston stopper impacts or contacts during axial motion toward the open end of the syringe barrel, whereby unintended withdrawal of the piston stopper from the syringe cylinder is prevented. This known stop element formed in the known syringe as a projection, which is in one piece with a finger support, is clamped on the syringe body laterally, so that the projection is inside on the wall of the syringe body in the mounted state. However there is a danger that sufficient fixing of the finger support is not guaranteed based on the clipping of the stop element and the finger support in one piece with it on the syringe body, so that correspondingly the syringe cannot be reliably manipulated by the user, especially during the injection process, and correspondingly can also slip.

U.S. Pat. No. 5,700,247 discloses a syringe, which has a finger support with integrated backstop-function. This finger support is a separate injection molded part, which comprises a base and cover plate, which is pushed on the corresponding DIN grip plate of the syringe body from the outside. The base plate reduced in diameter has a backstop function, which prevents the piston stopper from being erroneously removed from the syringe.

U.S. Pat. No. 4,909,788 and similarly U.S. Pat. No. 5,554,133 disclose a syringe with an elastomeric piston stopper, which has a gripping strip on its open end. An enlarged finger support can be mounted here at this open end, which locks in the said gripping strip, and is subsequently in a press fit, whereby it is can be rotated about the syringe axis.

U.S. Pat. No. 4,072,149 discloses a syringe with a plastic gripping strip, which extends into the syringe body and at the same time forms a stop element for the piston stopper.

Besides this backstop function the piston rod is secured against a rotation in the syringes, so that it cannot be removed in an unintended manner in use. In the process of so-called drawing or aspiration, in which the piston stopper is moved back and forth many times, for example during application of an aqueous solution in a container with a freeze-dried pharmaceutical substance, the piston rod can be lost from the threaded hole in the piston stopper. However this sort of prevention of rotation is not put into action in the above-described state of the art. However U.S. Pat. No. 4,711,637 describes a syringe having a piston rod with a cruciform cross-section, which includes means for prevention of rotation of the piston rod.

SUMMARY OF THE INVENTION

It is an object of the present invention to provide a syringe of the above-described type, which is formed so that the syringe has both a backstop function in regard to the piston stopper and rotational locking in regard to the piston rod.

It is another object of the present invention to provide a syringe of the above-described type having a piston stopper and a piston rod that screws into the piston stopper, which is formed so that the syringe has a stop to prevent unintended withdrawal of the piston stopper from the syringe barrel and means to limit rotation of the piston rod so that it cannot be unscrewed from the piston stopper.

These objects and others, which will be made more apparent hereinafter, are attained in a medicinal syringe comprising a syringe barrel made of glass or plastic, which is formed with a syringe head at one end of the syringe barrel, in which either a hollow syringe needle can be integrated or which has a Luer connection cone, and with a grip plate at an open end of the syringe barrel;

an elastomeric piston stopper and a piston rod, the piston stopper being insertable in the syringe barrel and provided with a threaded blind hole for screw connection with the piston rod, and the piston rod having a cruciform cross-section; and a stop element for preventing unintended withdrawal of the piston stopper from the syringe barrel.

According to the invention a plastic part attachable to the grip plate is provided at the open end remote from the syringe head. This plastic part comprises a retaining section for holding the syringe barrel, a hood-shaped section enlarged in relation to the grip plate so as to form an enlarged finger support and two one-piece snap catches formed on opposite sides of the hood-shaped section, in such manner that, when the plastic part is attached over the grip plate, the snap catches are in the vicinity of the open end of the syringe barrel, and the snap catches move and snap on an interior side of the syringe barrel; so that the stop element is thereby formed, preventing unintended withdrawal of the piston stopper and further preventing rotation of the piston rod through an angle of more than 90°.

By the features according to the invention a single simple plastic part can perform a backstop function and also prevent rotation of a piston rod with a cruciform cross-section, i.e. it has an integrated backstop function. The snap catches narrow or reduce the diameter of the syringe cylinder at its open end at two positions, so that rotation of the piston rod on account of its cruciform cross-section with a filling curvature, which fits the inner diameter of the syringe cylinder, is not more than 90°. At the same time the inserted snap catches act as stop elements to prevent the unintended withdrawal of the piston stopper. Since the snap catches are only inserted to a slight or small depth in the syringe barrel or cylinder, the siliconization applied to the interior cylinder wall is not impaired.

Preferably the plastic part is formed as a one-piece part. However in other embodiments it can comprise several individual parts.

For manufacture of the plastic part and/or its individual components all conventional shaping methods must be considered.

Since the above-mentioned medicinal syringes are a mass produced article, manufacturing costs of this syringe are a significant consideration. The additional costs for the separately made plastic part can be kept low, when the plastic part is an injection molded part, which can be made with reduced cost in large quantities.

When the grip plate according to DIN ISO 11040 is formed as a small strip, then the enlarged hood-shaped section of the plastic part extending from the grip plate can also be formed as a small strip, whose width is equal to that of the grip plate and whose length forming the widened finger support is larger than that of the DIN grip plate. Because of these features one and the same plastic part can provide an improved finger support besides preventing rotation of the piston rod and providing the backstop function.

In order to permit an easily gripped handling of the syringe, the ends of the finger support strip protruding beyond the DIN grip plate can be rounded.

BRIEF DESCRIPTION OF THE SEVERAL VIEWS OF THE DRAWING

The objects, features and advantages of the invention will now be illustrated in more detail with the aid of the following pre-fillable syringe with separate plastic part providing rotational locking and a backstop function according to the invention, with reference to the accompanying figures 3 in which:

FIG. 1 is a side elevational view of a pre-fillable syringe according to the invention as seen in the direction of the largest dimension or extent of the grip plate;

FIG. 2 is a side elevational view of the pre-fillable syringe shown in FIG. 1 as seen in a direction perpendicular to the largest dimension or extent of the grip plate;

FIG. 3 is a bottom plan view of the finger-support end of the syringe according to FIG. 1 with the piston stopper and piston rod removed.

DETAILED DESCRIPTION OF THE INVENTION

The syringe or injector according to FIGS. 1 to 3 is a standard pre-filled syringe with a clindrical syringe barrel 1, on which a syringe head 1a is formed at one end. In the present example a Luer cone and/or a Luer lock for a lockable conical connection is formed. However it is also possible that a hollow syringe needle is integrated in the syringe head 1a.

Figure 5:
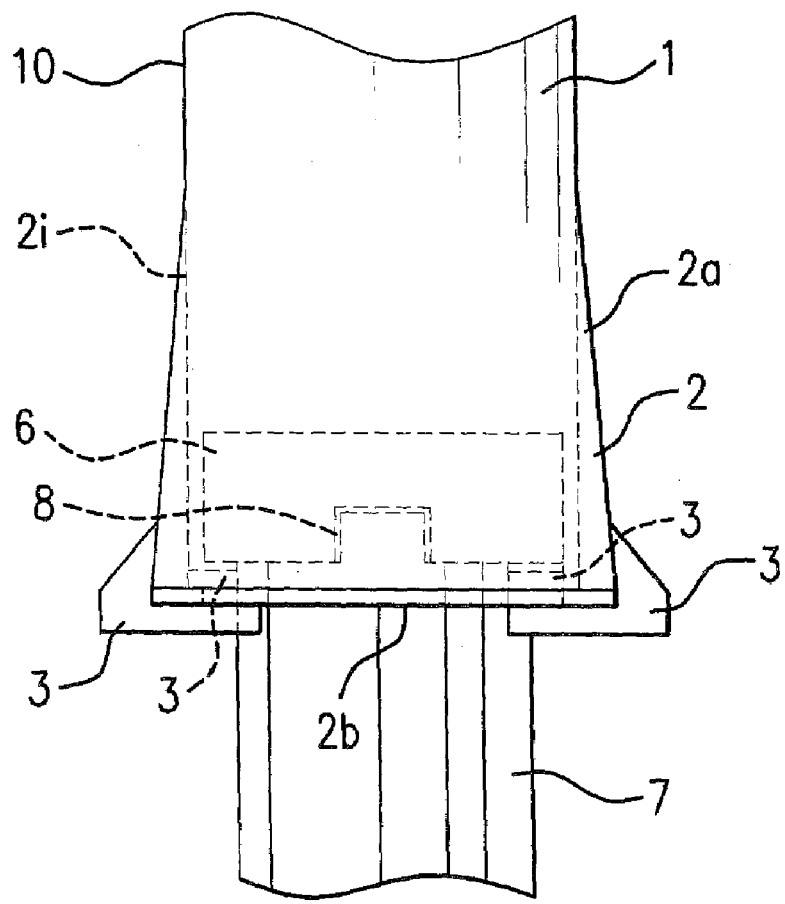
FIG. 5 is a detailed cutaway side view of the finger-support end of the syringe with the piston stopper drawn back so that it rests on the snap catches and cannot be withdrawn from the syringe barrel.

A DIN grip plate 4 is formed in one piece on the opposite open end of the syringe barrel 1. This open end of the filled syringe barrel 1 is thus closed with a piston stopper 6 made from elastomeric material with outer packing ribs, in which a standard piston rod 7 with a cruciform cross section and a disk-shaped fangerplate is screwed, as shown with dashed lines in FIG. 1 and FIG. 2. The piston rod 7 is screwed in a blind hole 8, shown in FIG. 5, provided for that purpose in the piston stopper 6. So that the piston stopper 6 is easily slidable on the interior wall of the syringe barrel 1 in use, it is provided with an interior siliconization.

So far the structure of the known medicinal syringe has been described.

A plastic part 2 is provided to guarantee that the piston rod 7 is secured to prevent rotation and to provide a backstop function for preventing removal of the piston stopper 6 from the syringe barrel 1. This plastic part 2 has a front-side retaining section 2a, which is provided with a through-going central passage with a cylindrical Inner surface 2i so that it can be retained and bear on an outer surface 1o of the syringe barrel 1, and a hood-shaped section 2b enlarged at the grip plate 4 in order to form an enlarged finger support. Two snap catches 3 are formed in one piece with this hood-shaped section 2b on opposite sides of it and are located in the vicinity of the open end of the syringe barrel 1 when the plastic part 2 is attached to the syringe barrel 1. The enlarged hood-shaped section 2b of the plastic part 2 is constructed to fit on the DIN grip plate. The width w of the hood-shaped section 2b is equal to that of the grip plate 4 and its length I is larger than that of the grip plate, so that an enlarged fingerplate is formed, as shown in FIG. 3. In order to guarantee good handling of the syringe, the ends of the finger support strip protruding beyond the DIN grip plate 4 are rounded.

The separate plastic part 2 is thus preferably an injection-molded part, which is made with reduced cost.

The injection molded plastic part 2 is pushed on the syringe from above, i.e. from the head side of the syringe after the labeling process. The axial height of the plastic part 2 is kept as small as possible so that it does not cover the label applied to the syringe barrel. The snap catches 3 molded on for rotational locking are pushed over the straight long sides of the grip plate 4 and snapped on the inner side of the syringe barrel (see FIGS. 2 and 3). Since the snap catches 3 have only a small insertion depth in the syringe barrel or cylinder 1, the siliconization applied to the interior cylinder wall is advantageously not damaged.

Figure 4:
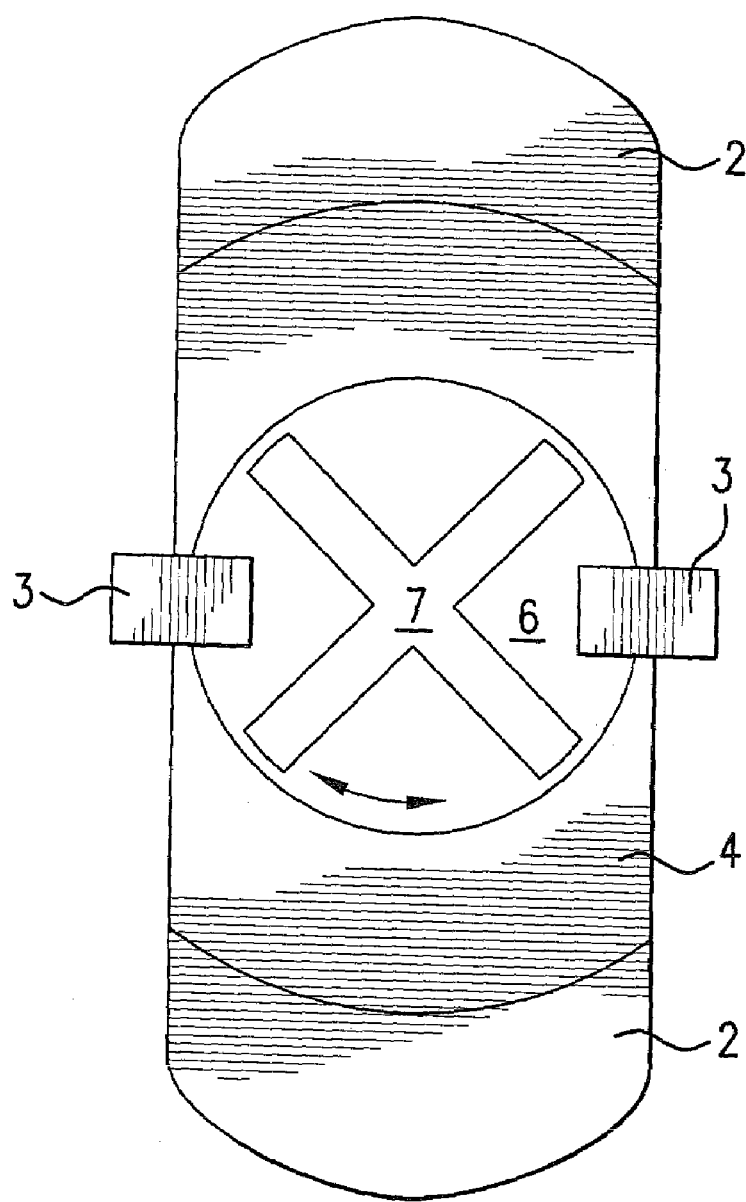
FIG. 4 is a bottom plan view of the syringe according to FIG. 1 with the piston stopper and cruciform piston rod in the syringe barrel, which shows how rotation of the piston rod over an anale greater than 90° is prevented.

The snap catches 3 narrow, as shown especially in FIG. 2, the interior diameter of the syringe cylinder or barrel. Thus they limit the rotation angle for rotation of the cruciform-cross-sectioned piston rod, i.e. they prevent rotation of the piston rod 7 beyond 90°, as shown especially in FIG. 4. Thus it is guaranteed that the piston rod 7 cannot be rotated out of the piston stopper 6. even during an emergency medication process.

The front ends of the snap catches 3 projecting into the syringe cylinder act as a stop for the piston stopper 6, i.e. they guarantee a backstop function, as shown particularly in FIG. 5.

The front ends of the snap catches 3 projecting into the syringe cylinder act as a stop for the piston stopper 6, i.e. they guarantee a backstop function.

The simply constructed plastic part 2 advantageously fulfills three functions:
prevention of withdrawal of the piston stopper 6 from the syringe barrel 1,
prevention of rotation of the piston rod 7 out from the piston stopper 6, and
an enlarged finger support.

The disclosure in German Patent Application 102 52 220.0 of Nov. 11, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a medicinal syringe, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A medicinal syringe comprising:
a cylindrical syringe barrel (1) made of glass or plastic, said cylindrical syringe barrel including a syringe head (1a) at one end of the cylindrical syringe barrel and a grip plate (4) at another open end of the syringe barrel, said another open end being remote from said one end of the cylindrical syringe barrel, said syringe head (1a) having a Luer connection cone or a hollow syringe needle integratable therein, said grip plate (4) being formed as a small strip with a width and a length;
an elastomeric piston stopper (6) and a piston rod (7), said piston stopper being insertable in the cylindrical syringe barrel (1) and provided with a threaded blind hole (8) for screw connection with said piston rod, said piston rod having a cruciform cross-section; and
a plastic part (2) fitting with said grip plate (4) at said open end remote from said syringe head (1a), said plastic part (2) comprising a retaining section (2a), a hood-shaped section (2b) that fits on said grip plate (4), and two one-piece snap catches (3) on opposite long sides of the hood-shaped section (2b) and in one piece therewith;
in which said retaining section (2a) is provided with a through-going central passage having a cylindrical inner surface (2i), said hood-shaped section (2b) fits on said grip plate (4) so that said hood-shaped section (2b) protrudes and extends laterally and outwardly beyond said grip plate (4) to form an enlarged finger support together with said grip plate (4), said enlarged finger support having a length (I) that is larger than said length of said grip plate (4);
so that, when said plastic part (2) is placed on said grip plate (4), said retaining section (2a) extends from said open end remote from said syringe head (1a) toward said syringe head with said cylindrical inner surface (2i) bearing on an outer surface (1o) of the cylindrical syringe barrel (1) and said snap catches (3) engage over straight sides of said grip plate (4) and snap on an inner side of the syringe barrel (1);
whereby said plastic part (2) prevents unintended withdrawal of the piston stopper and rotation of the piston rod through an angle of more than 90° while at the same time providing the enlarged finger support.

2. The medicinal syringe as defined in claim 1, wherein said grip plate (4) is formed according to DIN ISO 11040.

3. The medicinal syringe as defined in claim 1, wherein said grip plate (4) has a width (w) that is equal to that of the hood-shaped section (2b) of the plastic part (2).

4. The medicinal syringe as defined in claim 1, wherein opposite ends of the hood-shaped section (2b), which extend beyond said grip plate (4), are rounded.

5. The medicinal syringe as defined in claim 1, wherein said plastic part (2) is formed in one piece as an injection molded part.

6. The medicinal syringe as defined in claim 1, wherein said plastic part (2) comprises separate components that are connected with each other.

7. The medicinal syringe as defined in claim 6, wherein said separate components are injection molded parts.

8. The medicinal syringe as defined in claim 1, wherein said enlarged finger support has a width (w) equal to said width of said grip plate (4).

* * * * *